United States Patent
Yamada et al.

[11] Patent Number: 5,981,794
[45] Date of Patent: Nov. 9, 1999

[54] γ-OXO-HOMOPHENYLALANINE DERIVATIVES AND PROCESS FOR PRODUCING HOMOPHENYLALANINE DERIVATIVES BY REDUCING THE SAME

[75] Inventors: Masahiko Yamada, Kobe; Nobuo Nagashima, Takasago; Junzo Hasegawa, Akashi, all of Japan

[73] Assignee: Kaneka Corporation, Osaka, Japan

[21] Appl. No.: 09/171,170

[22] PCT Filed: Feb. 13, 1998

[86] PCT No.: PCT/JP98/00580

§ 371 Date: Dec. 3, 1998

§ 102(e) Date: Dec. 3, 1998

[87] PCT Pub. No.: WO98/35934

PCT Pub. Date: Aug. 20, 1998

[30] Foreign Application Priority Data

Feb. 14, 1997 [JP] Japan ................................ 9-047399
Dec. 18, 1997 [JP] Japan ................................ 9-365161

[51] Int. Cl.$^6$ ................ C07C 205/06; C07C 229/28
[52] U.S. Cl. ................ 562/437; 562/443; 562/445; 562/449
[58] Field of Search ................ 562/437, 443, 562/445, 449

[56] References Cited

U.S. PATENT DOCUMENTS 4,686,084  8/1987  Geke et al. ................ 422/17

OTHER PUBLICATIONS

Database CAPLUS on STN, Acc. No. 1997:749970, Griesbeck et al., 'A simple approach to beta amino acids by acylation of arenes with N–acylaspartic anhydrides.' Synlett (1997), (11), pp. 1243–1244. abstract, 1997.

*Primary Examiner*—Gary Geist
*Assistant Examiner*—Brian J. Davis
*Attorney, Agent, or Firm*—Pollock, Vande Sande & Amernick

[57] ABSTRACT

The present invention provides an economically advantageous and efficient process for producing an optically active homophenylalanine derivative of the general formula (IV), and an intermediate therefor and a process for producing it. The present invention relates to a process for producing homophenylalanine derivative of the general formula (IV) which comprises reacting a β-benzoylacrylic acid derivative of the general formula (II) with a 1-arylethylamine derivative of the general formula (III) and reducing the resultant γ-oxo-homophenylalanine derivative of the general formula (I).

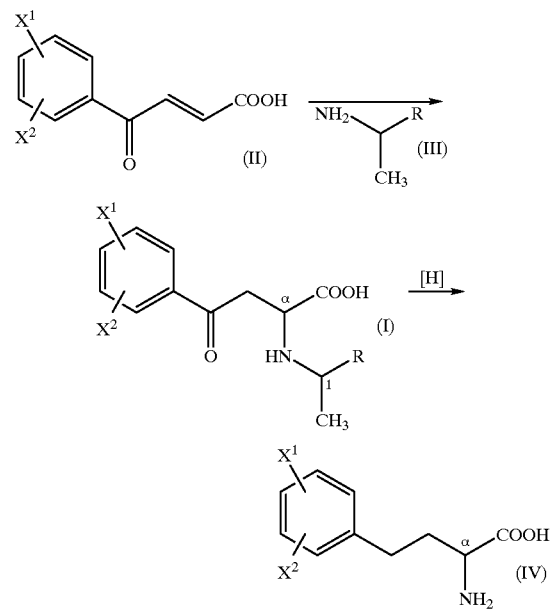

23 Claims, No Drawings

γ-OXO-HOMOPHENYLALANINE DERIVATIVES AND PROCESS FOR PRODUCING HOMOPHENYLALANINE DERIVATIVES BY REDUCING THE SAME

TECHNICAL FIELD

The present invention relates to a process for producing an optically active homophenylalanine derivative of the general formula (IV):

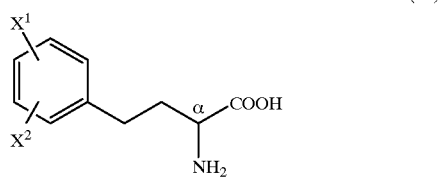

(wherein $X^1$ and $X^2$ are the same or different and each represents a hydrogen atom, an alkyl group 1 to 7 carbon atoms, an aryl group containing 6 to 10 carbon atoms, an aralkyl group containing 7 to 10 carbon atoms, a hydroxyl group, a halogen atom, a cyano group, a trifluoromethyl group, an alkoxyl group containing 1 to 4 carbon atoms, an alkylmercapto group containing 1 to 4 carbon atoms or a nitro group), to an intermediate therefor, namely a γ-oxo-homophenylalanine derivative, and to a process for the production thereof.

The optically active homophenylalanine derivative which is represented by the above general formula (IV) (hereinafter referred to as "homophenylalanine derivative (IV)") is an amino acid that is very important as a constituent of medicinals, in particular an angiotensin converting enzyme inhibitor (hereinafter referred to as "ACE inhibitor").

As is described in Japanese Kokai Publication Sho-64-71934, the above-mentioned homophenylalanine derivative (IV) can be readily derived into said ACE inhibitor following conversion of its amino group to a hydroxy group by reaction with nitrous acid.

BACKGROUND ART

Among the so-far known processes for producing the above-mentioned optically active homophenylalanine derivative (IV), there is a process using a biocatalyst such as an enzyme, and the process employing the so-called asymmetric synthesis without using any biocatalyst such as an enzyme.

As the above-mentioned process using a biocatalyst, Japanese Kokai Publication Hei-01-79134, for instance, discloses a process involving asymmetric decomposition of a corresponding hydantoin with hydantoinase, and Japanese Kokai Publication Hei-02-31694 discloses a process comprising asymmetrically hydrolyzing a corresponding amino-nitrile with nitrile hydrolase. These processes, however, require the use of a toxic hydrocyanic acid compound in raw material synthesis.

U.S. Pat. No. 5,316,943 discloses a process comprising trans-amination of a corresponding keto acid with transaminase and, in the Journal of Organic Chemistry, vol. 55, page 5567 (1990), there is disclosed a process comprising reductively aminating a corresponding keto acid using phenylalanine dehydrogenase. These processes, however, require the use of an expensive keto acid as a material.

In the Journal of the American Chemical Society, vol. 112, page 945 (1990), there is disclosed a process which comprises asymmetrically hydrolyzing a corresponding ester using an enzyme and, in the Bulletin of the Chemical Society of Japan, vol. 55, page 918 (1982), there is disclosed a process comprising asymmetrically hydrolyzing a corresponding acetyl derivative using acylase. These processes, however, are processes for racemic resolution, hence, theoretically, the desired compounds can be obtained only in half amounts relative to the total amounts of starting racemates. Another disadvantage lies, for example, in the complexity of operational procedure.

As the above-mentioned process comprising asymmetric synthesis, there may be mentioned the process in which a chloroacetyl containing compound is reduced with an asymmetric boron complex followed by rearrangement (the Journal of the American Chemical Society, vol. 114, page 1906 (1992)), the process comprising hydrogenating a 4-phenyl-2-aminocrotonic acid derivative with an asymmetric rhodium complex (the Journal of Organic Chemistry, vol. 52, page 5142 (1987)) and the process comprising reacting an optically active glycine derivative with phenylpropyl bromide (the Journal of the American Chemical Society, vol. 108, page 1103 (1986)), among others. These processes for asymmetric synthesis, however, require the use of an expensive catalyst or an organometallic compound difficult to handle.

As the above-mentioned process comprising optical resolution of the optically active homophenylalanine derivative (IV), there may be mentioned, for example, the process comprising resolving a corresponding N-formyl derivative using phenethylamine (Japanese Kokai Publication Sho-63-63646), the process comprising resolving a corresponding methyl ester using mandelic acid (Japanese Kokai Publication Sho-63-145256) and the process comprising resolving a corresponding N-acetyl compound using brucine (the Journal of Biological Chemistry, vol. 122, page 348 (1937 to 1938)), among others. Theoretically, however, these processes can give the desired compounds only in half of the total amounts of starting racemic mixture and are also disadvantageous in that their operational procedures are complicated.

The so-far known processes thus cannot necessarily be said to be satisfactory.

In view of the foregoing, it is an object of the present invention to provide an economically advantageous and efficient process for producing the above-mentioned optically active homophenylalanine derivative (IV), and an intermediate therefor and a process for producing it.

SUMMARY OF THE INVENTION

The present invention relates to a γ-oxo-homophenylalanine derivative of the general formula (I):

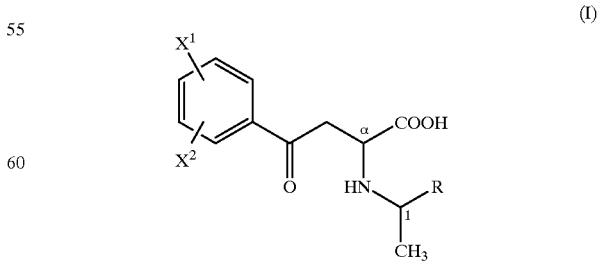

(wherein $X^1$ and $X^2$ are the same or different and each represents a hydrogen atom, an alkyl group containing 1 to 7 carbon atoms, an aryl group containing 6 to 10 carbon atoms, an aralkyl group containing 7 to 10 carbon atoms, a hydroxyl group, a halogen atom, a cyano group, a trifluoromethyl group, an alkoxyl group containing 1 to 4 carbon atoms, an alkylmercapto group containing 1 to 4 carbon atoms or a nitro group, and R represents a phenyl group, a substituted phenyl group or a naphthyl group) (hereinafter referred to as "γ-oxo-homophenylalanine derivative (I)").

The present invention also relates to a process for producing a γ-oxo-homophenylalanine derivative (I) which comprises reacting a β-benzoylacrylic acid derivative of the general formula (II):

(wherein $X^1$ and $X^2$ are as defined above) (hereinafter referred to as "β-benzoylacrylic acid derivative (II)") with a 1-arylethylamine derivative of the general formula (III):

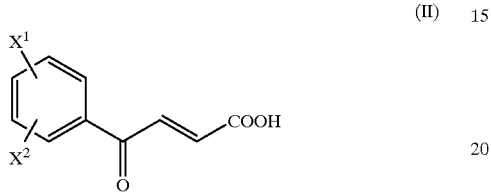

(wherein R is as defined above) (hereinafter referred to as "1-arylethylamine derivative (III)").

The present invention further relates to a process for producing said homophenylalanine derivative (IV) which comprises subjecting said γ-oxo-homophenylalanine derivative (I) to reduction reaction.

DETAILED DESCRIPTION OF THE INVENTION

The present invention is described in further detail in the following.

According to the present invention, the γ-oxo-homophenylalanine derivative (I), which is novel substance and can easily be prepared by the so-called Michael addition reaction from the above-mentioned β-benzoylacrylic acid derivative (II) and the above-mentioned 1-arylethylamine derivative (III), is used as an intermediate, and the above-mentioned homophenylalanine derivative (IV) can easily be produced by reducing said γ-oxo-homophenylalanine derivative (I) in the presence of a metal catalyst.

According to the present invention, when the optically active 1-arylethylamine derivative (III) mentioned above is used in the above-mentioned addition reaction, the γ-oxo-homophenylalanine derivative is formed diastereoselectively as a precipitate and, therefore, an (R)-homophenylalanine derivative or a (S)-homophenylalanine derivative can be produced with very high optical purity by reducing said γ-oxo-homophenylalanine derivative.

The reactions involved in the present invention can be shown below in terms of reaction formula as follows:

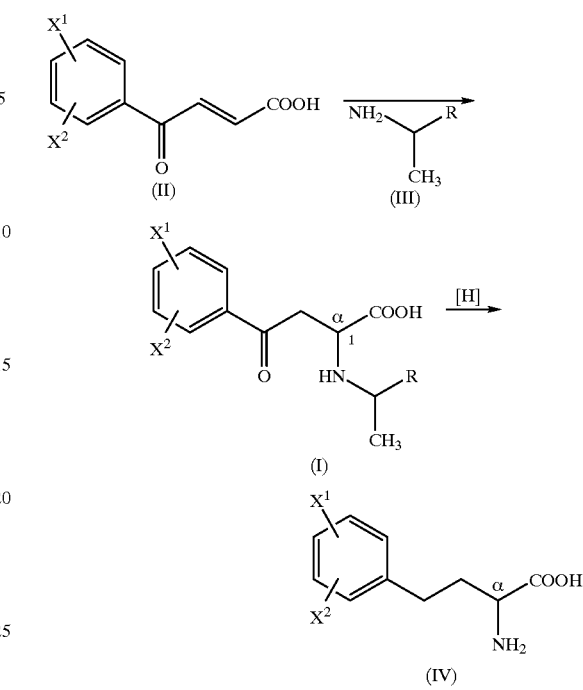

In the practice of the present invention, examples of the above-mentioned β-benzoylacrylic acid derivative (II), which are preferred based on the utility of the obtained homophenylalanine derivative (IV), are p-methoxy-β-benzoylacrylic acid in which $X^1$ is a p-methoxy group and $X^2$ is a hydrogen atom, and unsubstituted β-benzoylacrylic acid in which $X^1$ is a hydrogen atom and $X^2$ is a hydrogen atom.

For said β-benzoylacrylic acid derivative (II), there exist the trans form and the cis form.

Said trans form can easily be synthesized by a known method, for example by the Friedel-Crafts reaction from an aromatic compound and maleic anhydride (Organic Reactions, vol. 5, page 229 (1957)) or by dehydration condensation of an acetophenone derivative and glyoxylic acid (Japanese Kokai Publication Sho-52-39020).

Said cis form can be prepared, for instance, by isomerization of the trans form by light irradiation.

Said trans form and cis form isomers both can be used in the Michael addition reaction according to the present invention. However, the trans form, which is low in processing degree, is preferred from the viewpoint of industrial utility.

In the practice of the present invention, 1-phenethylamine is preferred as the 1-arylethylamine derivative (III), since it is the most inexpensive one. Furthermore, the optically active γ-oxo-homophenylalanine derivative can be obtained by using (S)-1-phenethylamine or (R)-1-phenethylamine.

Said 1-arylethylamine derivative (III) may be a commercial product as it is or a product purified therefrom by distillation, for instance.

In the practice of the present invention, the process for producing the γ-oxo-homophenylalanine derivative (I) by subjecting said β-benzoylacrylic acid derivative (II) and said 1-arylethylamine derivative (III) to addition reaction may comprise, for example, mixing said β-benzoylacrylic acid derivative (II) and said 1-arylethylamine derivative (III) in a solvent and allowing the reaction to proceed. More specifically, there may be mentioned, for example, the method comprising adding dropwise the 1-arylethylamine derivative (III) to an ethanol solution of the β-benzoylacrylic acid derivative (II).

When, in producing the γ-oxo-homophenylalanine derivative (I) by the addition reaction mentioned above, the (S)-form of 1-phenethylamine is used, for instance, a mixture of two diastereomers is formed, namely a γ-oxo-homophenylalanine derivative having the (αS,1S) configuration as represented by the general formula (V):

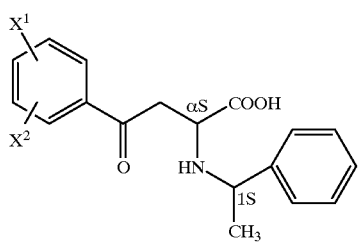

(V)

(wherein $X^1$ and $X^2$ are as defined above) and a γ-oxo-homophenylalanine derivative having the (αR,1S) configuration as represented by the general formula (VI):

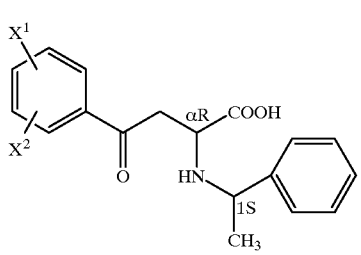

(VI)

(wherein $X^1$ and $X^2$ are as defined above).

In the above addition reaction, the diastereomer ratio ((αS,1S):(αR,1S)) is generally about (51 to 99%):(49 to 1%). The (αS,1S) form is less soluble in organic solvents and, therefore, the (αS,1S) form can be obtained with a diastereomer ratio of not less than 70% by filtration of the precipitate resulting from the reaction mixture when an appropriate solvent system is selected. Furthermore, it is also possible to obtain the (αS,1S) form with a diastereoselectivity of not less than 95% by selecting the reaction conditions, for example, raising the reaction temperature.

By using the (R)-form of 1-phenethylamine, it is also possible to selectively obtain a γ-oxo-homophenylalanine derivative having the (αR,1R) configuration similarly with a ratio of not less than 95% to the (αS,1R) form.

As the solvent to be used in the above addition reaction, there may be mentioned, for example, aqueous solvents; alcohol solvents, such as methanol, ethanol, isopropanol, n-propanol, t-butyl alcohol, n-hexanol, etc.; nitrile solvents such as acetonitrile, propionitrile, etc.; ether solvents such as diethyl ether, dioxane, tetrahydrofuran, etc.; amide solvents such as dimethylformamide, dimethylacetamide, hexamethylphosphoramide, N-methylpyrrolidone, etc.; halogenated hydrocarbon solvents such as methylene chloride, chloroform, etc.; ketone solvents such as acetone, methyl ethyl ketone, methyl t-butyl ketone, etc.; sulfoxide or sulfone solvents such as dimethyl sulfoxide, sulfolane, etc.; ester solvents such as ethyl acetate, methyl acetate, etc.; aromatic hydrocarbon solvents such as benzene, toluene, xylene, etc.; aliphatic hydrocarbon solvents such as hexane, pentane, cyclohexane, etc.; and mixtures of these.

When a highly hydrophobic solvent is used in the above addition reaction, the diastereomer ratio of the γ-oxo-homophenylalanine derivative obtained will be not more than 70% and this is unfavorable from the viewpoint of yield. In a strongly hydrophilic solvent, the progress of the reaction is rather slow. In view of these, protic solvents, in particular alcohol solvents such as ethanol, n-propanol and i-propanol, are preferred and a diastereomer ratio of not less than 80% can be attained by using these.

In the above addition reaction, the mixing ratio between the above-mentioned β-benzoylacrylic acid derivative (II) and the above-mentioned 1-arylethylamine derivative (III) is generally β-benzoylacrylic acid derivative (II):1-arylethylamine derivative (III) =about 3:1 to 1:3. Since, however, the reaction rate is faster when the 1-arylethylamine derivative (III) is in excess as compared with the β-benzoylacrylic acid derivative (II), a ratio of 1:1 to 1:1.5 is preferred.

The reaction temperature in the above addition reaction is preferably 0 to 80° C. From the viewpoint of the shortening of reaction time, 30 to 60° C. is more preferred.

The concentration in the above addition reaction is preferably 0.1 to 20% for the β-benzoylacrylic acid derivative (II). Since, however, the reaction rate is slow at a smaller concentration, 1 to 20% is more preferred. For controlling the reaction, for example to expedite the reaction in the early stage and thereafter obtain a diastereomer selectively, the production can also be carried out by controlling the reaction concentration, for example in a manner such that the reaction between β-benzoylacrylic acid derivative (II) and 1-arylethylamine (III) is carried out at a concentration of 2% for the first 5 hours and then dilution is made to 1%.

Since the above addition reaction is accelerated under basic conditions, a base may be added as an additive to the reaction mixture. As said base, there may be mentioned, for example, amines such as triethylamine, trimethylamine, diisopropylamine, diazabicyclooctane, etc.; alkali metal carbonates such as sodium bicarbonate, potassium bicarbonate, sodium carbonate, potassium carbonate, etc.; alkali metal hydroxides such as sodium hydroxide, potassium hydroxide, lithium hydroxide, etc.; alkaline earth metal hydroxides such as calcium hydroxide, magnesium hydroxide, barium hydroxide, etc.; transition metal hydroxides such as iron hydroxide, zinc hydroxide, etc.; quaternary ammonium hydroxides such as tetramethylammonium hydroxide, tetraethylammonium hydroxide, benzyltrimethylammonium hydroxide, etc.: and the like.

In the above addition reaction, the desired product, namely the γ-oxo-homophenylalanine derivative (I) can be isolated, for instance, by filtering off the desired product formed as a precipitate during the reaction. The filtration may be performed after heating and concentrating the reaction mixture. Further purification may be carried out by fractionation by column chromatography or HPLC or by recrystallization using an acetonitrile-water system, for instance, as a solvent. It is also possible to isolate said desired product after conversion to the corresponding hydrochloride, sulfate or the like by adding an acid such as hydrochloric acid or sulfuric acid to the reaction system without delay after the above addition reaction.

It is also possible to carry out the next reduction procedure after adding sulfuric acid or hydrochloric acid in an amount not less than an equivalent to the γ-oxo-homophenylalanine derivative (I) formed by the above addition reaction.

In accordance with the present invention, the above-mentioned homophenylalanine derivative (IV) can be obtained by subjecting the above γ-oxo-homophenylalanine derivative (I) to reduction reaction.

As the reaction to be used for said reduction reaction, there may be mentioned, for example, the catalytic reduction reaction in the presence of a metal catalyst; the so-called Clemmensen reduction reaction in an acidic solvent in the presence of a metal such as zinc, zinc amalgam, mercury or tin or the like; the reduction reaction using hydrazine; the reduction reaction using a silicon hydride compound; the reduction reaction comprising converting the ketone to a thioketal and then reducing the latter using Raney nickel; the reduction reaction comprising converting the ketone to a corresponding tosylhydrazone and then reducing the same with sodium borohydride; the reduction reaction comprising once reducing the ketone with a metal hydride and then conducting further reduction in the presence of a metal catalyst.

Among them, the catalytic reduction reaction in the presence of a metal catalyst is preferred because of inexpensiveness.

As the metal catalyst to be used in said catalytic reduction reaction, there may be mentioned, for example, palladium catalysts such as palladium-carbon, palladium hydroxide, palladium oxide, Pd—BaSO$_4$, Pd—CaCO$_3$, Pd—Al$_2$O$_3$, palladium-triphenylphosphine, Pd[P(C$_6$H$_5$)$_3$]$_4$, Lindlar catalyst colloidal palladium, etc.; platinum catalysts such as platinum oxide, platinum-carbon, etc.; nickel catalysts such as Raney nickel etc.; zinc catalysts such as zinc powder; and the like. Among them, palladium catalysts are preferred since they can give the products in high yields. In particular, palladium-carbon is preferred from the viewpoint of selectivity.

In the above catalytic reduction reaction, a reducing agent such as mentioned below can be used. As the reducing agent, there may be mentioned, for example, hydrogen; formic acid, formic acid salts; metal hydrides; metals such as zinc, zinc amalgam, mercury, tin, etc.; hydrazine; silicon hydride compounds; Raney nickel, and the like. Among them, hydrogen, formic acid, formic acid salts and metal hydrides are preferred because of inexpensiveness.

As said formic acid salts, there may be mentioned, for example, ammonium formate, sodium formate, triethylammonium formate and the like.

As said metal hydrides, there may be mentioned, for example, sodium borohydride, NaB(CN)H$_3$, and the like.

The above reduction reaction can proceed mildly and in good yields when it is carried out in a polar protic solvent in the presence of an acid, for instance.

As said acid, there may be mentioned, for example, mineral acids such as sulfuric acid, hydrochloric acid and phosphoric acid. The addition level of said acid is preferably about 1 to 30 equivalents relative to the γ-oxo-homophenylalanine derivative (I). When it is below 1 equivalent, the reduction reaction will not proceed to a satisfactory extent in some instances. When it exceeds 30 equivalents, the postreaction treatment becomes complicated.

As said polar protic solvent, there may be mentioned, for example, water, alcohol, acetic acid, and mixtures of these. From the viewpoint of operability, alcoholic solvents such as methanol, ethanol, n-propanol and i-propanol are preferred.

As an example of the above reduction reaction, the reaction to be carried out in a mineral acidcontaining alcohol solvent using hydrogen as the reducing agent is explained in the following.

To (αR,1R)-N-(1-phenethyl)-γ-oxo-p-methoxyhomophenylalanine is added about 1 to 100% of palladium-carbon as the catalyst, and the reaction is carried out at 0 to 100° C., preferably at 5 to 70° C., using hydrogen as the reducing agent and an alcoholic solvent, such as ethanol, as the solvent, in the presence of an acid such as a mineral acid as mentioned above, for several to 80 hours with stirring, whereby almost quantitative conversion to (R)-p-methoxyhomophenylalanine can be attained. It is also possible to reduce the reaction time by increasing the amount of the catalyst.

In the above catalytic reduction reaction, the asymmetry at position of the γ-oxo-homophenylalanine derivative (I) is retained. Therefore, a homophenylalanine derivative having the (S) configuration at a position can be synthesized from the corresponding γ-oxo-homophenylalanine derivative having the (αS,1S) configuration, and a homophenylalanine derivative having the (R) configuration at α position from a corresponding γ-oxo-homophenylalanine derivative having the (αR,1R) configuration.

After completion of the above catalytic reduction reaction, the catalyst is separated, and then the solvent is removed, and the homophenylalanine derivative (IV) can be obtained as highly pure crystals. If necessary, they can be recrystallized using a solvent such as an ethanol-water system, for instance. Further, they can be purified also by using an ion exchange resin such as a cation exchange resin or by reversed phase chromatography, for instance.

The optically active homophenylalanine derivative (IV) obtained in the above manner can easily be derived into the ACE inhibitor mentioned above by a conventional method generally used in peptide synthesis, such as the acid chloride method, NCA method, active ester method or mixed acid anhydride method, or after conversion to the hydroxy form.

In accordance with the present invention, the γ-oxo-homophenylalanine derivative (I) can be obtained diastereoselectively and in very high yields from the β-benzoylacrylic acid derivative (II) and the optically active 1-arylethylamine derivative (III), which are inexpensive, by adapting the Michael addition reaction and the treatment method therefor, and further said derivative (I) can be derived by reduction into the optically active homophenylalanine derivative (IV) in high yields.

MODES FOR CARRYING OUT THE INVENTION

The following examples illustrate the present invention in further detail. They are, however, by no means limitative of the scope of the present invention.

EXAMPLE 1

Synthesis of (αR,1R)-N-(1-phenethyl)-γ-oxo-p-methoxy-homophenylalanine

Trans-p-methoxy-β-benzoylacrylic acid (206 mg) was dissolved in 20 mL of ethanol, and the temperature was adjusted to 40° C. (R)-1-Phenethylamine (121 mg, 1 equivalent) was added, and the reaction was carried out at 40° C. for 15 hours. The resulting precipitate was filtered off, recrystallized from acetonitrile-water, and then dried under vacuum to give 170 mg of (αR,1R)-N-(1-phenethyl)-γ-oxo-p-methoxy-homophenylalanine as white needle crystals (yield 52%).

TLC (silica gel); Rf=0.55 (n-butanol:acetic acid:water= 4:1:1).

NMR (DMSO-d$_6$, δ): 7.9 (d, J=7.5, 2H), 7.5 (m, 5H), 7.1 (d, J=7.5, 2H), 4.5 (q, J=6.8, 1H), 3.9 (s, 3H), 3.8 (m, 1H), 3.6 (m, 2H), 1.6 (d, J=6.8, 3H).

IR (KBr disk, cm$^{-1}$): 1680, 1600, 1570, 1380, 1250, 1180.

Melting point: 160 to 161° C. $[\alpha]^{20}_D$=−90.2 (c=0.051, MeOH:1 N H$_2$SO$_4$=3:1, v/v).

Elemental analysis: Found: C, 69.66; H, 6.53; N, 4.11; Calculated: C, 69.71; H, 6.47; N, 4.28.

EXAMPLE 2

Synthesis of (αR,1R)-N-(1-phenethyl)-γ-oxo-p-methoxy-homophenylalanine and (αS,1R)-N-(1-phenethyl)-γ-oxo-p-methoxy-homophenylalanine Trans-p-methoxy-β-benzoylacrylic acid (410 mg) was dissolved in 20 mL of ethanol, and the temperature was adjusted to 20° C. (R)-1-Phenethylamine (240 mg, 1 equivalent) was added, and the reaction was carried out at 20° C. for 15 hours. The resulting precipitate was filtered off and dried under vacuum to give a mixture of (αR,1R)-N-(1-phenethyl)-γ-oxo-p-methoxy-homophenylalanine and (αS,1R)-N-(1-phenethyl)-γ-oxo-p-methoxy-homophenylalanine as a white precipitate with a diastereomer ratio of 6:4. 370 mg of the white precipitate was yielded. The yield was 56% as the total of the two diastereomers. The (αS,1R) form was isolated and purified by HPLC. (αS,1R) form:

TLC (silica gel); Rf=0.55 (n-butanol:acetic acid:water=4:1:1).

NMR (DMSO-d$_6$, δ): 7.9 (d, J=7.5, 2H), 7.5 (m, 5H), 7.1 (d, J=7.5, 2H), 4.6 (q, J=6.8, 1H), 3.9 (s, 3H), 3.8 (m, 1H), 3.6 (m, 2H), 1.7 (d, J=6.8, 3H).

EXAMPLE 3

Synthesis of (αS,1S)-N-(1-phenethyl)-γ-oxo-p-methoxyhomophenylalanine

Trans-p-methoxy-β-benzoylacrylic acid (410 mg) was dissolved in 20 mL of ethanol, and the temperature was adjusted to 40° C. (S)-1-Phenethylamine (240 mg, 1 equivalent) was added, and the reaction was carried out at 40° C. for 5 hours. Ethanol (20 mL) was added to the reaction mixture and the reaction was continued for further 10 hours. The resulting precipitate was filtered off and dried under vacuum to give 380 mg of (αS,1S)-N-(1-phenethyl)-γ-oxo-p-methoxy-homophenylalanine as a white precipitate. The diastereomer ratio ((αS,1S) form/(αR,1S) form) was not less than 95/5 (yield 58%). The precipitate collected by filtration was recrystallized from acetonitrile-water to give (αS,1S)-N-(1-phenethyl)-γ-oxo-p-methoxy-homophenylalanine as white needle crystals.

TLC (silica gel); Rf=0.55 (n-butanol:acetic acid:water=4:1:1).

NMR (DMSO-d$_6$, δ): 7.9 (d, J=7.5, 2H), 7.5 (m, 5H), 7.1 (d, J=7.5, 2H), 4.5 (q, J=6.8, 1H), 3.9 (s, 3H), 3.8 (m, 1H), 3.6 (m, 2H), 1.6 (d, J=6.8, 3H).

IR (KBr disk, cm$^{-1}$): 1680, 1600, 1570, 1380, 1250, 1180.

Melting point: 160 to 161° C. $[\alpha]^{20}_D$=+90.1 (c=0.051, MeOH:1 N H$_2$SO$_4$=3:1, v/v).

Elemental analysis: Found: C, 69.76; H, 6.35; N, 4.12; Calculated: C, 69.71; H, 6.47; N, 4.28.

EXAMPLE 4

Synthesis of (αS,1S)-N-(1-phenethyl)-γ-oxo-p-methoxy-homophenylalanine

Trans-p-methoxy-β-benzoylacrylic acid (185 mg) was dissolved in 10 mL of ethanol, and the temperature was adjusted to 40° C. (S)-1-Phenethylamine (121 mg, 1.1 equivalent) was added, and the reaction was carried out at 40° C. for 15 hours. The resulting precipitate was filtered off and dried under vacuum to give 210 mg of (αS,1S)-N-(1-phenethyl)-γ-oxo-p-methoxy-homophenylalanine as a white precipitate. The yield was 71%. The diastereomer ratio ((αS,1S) form/(αR,1S) form) was not less than 95/5.

EXAMPLE 5

Synthesis of (αS,1S)-N-(1-phenethyl)-γ-oxo-p-methoxy-homophenylalanine

Trans-p-methoxy-β-benzoylacrylic acid (206 mg) was dissolved in 10 mL of ethanol, and the temperature was adjusted to 40° C. (S)-1-Phenethylamine (109 mg, 0.9 equivalent) was added, and the reaction was carried out at 40° C. for 15 hours. The resulting precipitate was filtered off and dried under vacuum to give 165 mg of (αS,1S)-N-(1-phenethyl)-γ-oxo-p-methoxy-homophenylalanine as a white precipitate. The yield was 42%. The diastereomer ratio between the (αS,1S) form and (αR,1S) form was about 85:15.

EXAMPLES 6 to 19

Synthesis of (αS,1S)-N-(1-phenethyl)-γ-oxo-p-methoxy-homophenylalanine and (αR,1S)-N-(1-phenethyl)-γ-oxo-p-methoxy-homophenylalanine Trans-p-methoxy-β-benzoylacrylic acid (20 mg) was dissolved in 2 mL of a solvent specified in Table 1, and the temperature was adjusted to 40° C. (S)-1-Phenethylamine (13 mg, 1.1 equivalents) was added, and the reaction was carried out at 40° C. for 15 hours. The whole reaction mixture was added to 18 mL of aqueous acetonitrile (acetonitrile:buffer solution (pH 2.5)=8:2, v/v) and analyzed by HPLC. (αaS,1S)-N-(1-phenethyl)-γ-oxo-p-methoxy-homophenylalanine and (αR,1S)-N-(1-phenethyl)-γ-oxo-p-methoxy-homophenylalanine were obtained with the yield and diastereomer ratio shown in Table 1.

In Table 1, the yield is for total of the two diastereomers.

TABLE 1

| | Solvent | Yield (%) | (αS, 1S) form: (αR, 1S) form ratio |
|---|---|---|---|
| Example 6 | Hexane | 45 | 53:47 |
| Example 7 | Toluene | 90 | 56:43 |
| Example 8 | Chloroform | 80 | 60:40 |
| Example 9 | Ethyl acetate | 90 | 59:41 |
| Example 10 | Tetrahydrofuran | 90 | 55:45 |
| Example 11 | 2-Propanol | 86 | 87:13 |
| Example 12 | 1-Propanol | 87 | 92:8 |
| Example 13 | Acetone | 40 | 62:38 |
| Example 14 | Ethanol | 90 | 70:30 |
| Example 15 | Methanol | 71 | 67:33 |
| Example 16 | DMF | 70 | 80:20 |
| Example 17 | Acetonitrile | 90 | 70:30 |
| Example 18 | Ethanol/water (1/1) | 67 | 91:9 |
| Example 19 | Acetonitrile/water (1/1) | 60 | 68:32 |

EXAMPLE 20

Synthesis of (αs,1S)-N-(1-phenethyl)-γ-oxo-p-methoxy-homophenylalanine

Trans-p-methoxy-β-benzoylacrylic acid (206 mg) was dissolved in 20 mL of ethanol, and the temperature was adjusted to 50° C. (S)-1-Phenethylamine (135 mg, 1.1 equivalents) was added, and the reaction was carried out at 50° C. for 15 hours. The resulting precipitate was filtered off and dried under vacuum to give 255 mg of (αS,1S)-N-(1-phenethyl)-γ-oxo-p-methoxy-homophenylalanine as a white precipitate. The yield was 78%. The diastereomer ratio ((αS,1S) form/(αR,1S) form) was not less than 95/5.

EXAMPLE 21

Synthesis of (αS,1S)-N-(1-phenethyl)-γ-oxo-p-methoxy-homophenylalanine

Trans-p-methoxy-β-benzoylacrylic acid (500 mg) was dissolved in 10 mL of ethanol, and the temperature was adjusted to 50° C. (S)-1-Phenethylamine (323 mg, 1.1 equivalents) was added, and the reaction was carried out at 50° C. for 15 hours. The resulting precipitate was filtered off and dried under vacuum to give 650 mg of (αS,1S)-N-(1-phenethyl)-γ-oxo-p-methoxy-homophenylalanine as a white precipitate. The yield was 83%. The diastereomer ratio ((αS,1S) form/(αR,1S) form) was not less than 95/5.

EXAMPLE 22

Synthesis of (αS,1S)-N-(1-phenethyl)-γ-oxo-p-methoxy-homophenylalanine

Trans-p-methoxy-β-benzoylacrylic acid (1.0 g) was dissolved in 10 mL of ethanol, and the temperature was adjusted to 50° C. (S)-1-Phenethylamine (646 mg, 1.1 equivalents) was added, and the reaction was carried out at 50° C. for 15 hours. The resulting precipitate was filtered off and dried under vacuum to give 1.27 g of (αS,1S)-N-(1-phenethyl)-γ-oxo-p-methoxy-homophenylalanine as a white precipitate. The yield was 80%. The diastereomer ratio ((αS,1S) form/(αR,1S) form) was not less than 95/5.

EXAMPLE 23

Synthesis of (αS,1S)-N-(1-phenethyl)-γ-oxo-homophenylalanine

Trans-β-benzoylacrylic acid (176 mg) was dissolved in 20 mL of ethanol, and the temperature was adjusted to 50° C. (S)-1-Phenethylamine (121 mg, 1 equivalent) was added, and the reaction was carried out at 50° C. for 15 hours. The resulting precipitate was filtered off and dried under vacuum to give 240 mg of a mixture of (αS,1S)-N-(1-phenethyl)-γ-oxo-homophenylalanine and (αR,1S)-N-(1-phenethyl)-γ-oxo-homophenylalanine as a white precipitate with a diastereomer ratio of about 90:10. The yield was 81%. Recrystallization from acetonitrile-water gave (αS,1S)-N-(1-phenethyl)-γ-oxo-homophenylalanine as white plate crystals.

TLC (silica gel); Rf=0.50 (n-butanol:acetic acid:water=4:1:1).

NMR (DMSO-$d_6$, δ): 7.9 (d, J=7.3, 2H), 7.6 (dd, J=7.3, 7.8, 1H), 7.5 (dd, J=7.3, 7.8, 2H), 7.3 (m, 5H), 4.6 (q, J=6.8, 1H), 3.8 (m, 1H), 3.6 (m, 2H), 1.7 (d, J=6.8, 3H).

IR (KBr disk, cm$^{-1}$): 1690, 1630, 1610, 1570, 1380.

Melting point: 178 to 179° C. (decomposition). $[α]^{20}_D$=+80.9 (c=0.047, MeOH:1 N $H_2SO_4$=3:1, v/v).

Elemental analysis: Found: C, 72.84; H, 6.53; N, 4.80; Calculated: C, 72.71; H, 6.44; N, 4.71.

EXAMPLE 24

Synthesis of (αS,1S)-N-(1-phenethyl)-γ-oxo-p-chloro-homophenylalanine

Trans-p-chloro-β-benzoylacrylic acid (210 mg) was dissolved in 5 mL of ethanol, and the temperature was adjusted to 60° C. (S)-1-Phenethylamine (144 mg, 1.2 equivalents) was added, and the reaction was carried out at 60° C. for 6 hours. The resulting precipitate was filtered off and dried under vacuum to give 280 mg of (αS,1S)-N-(1-phenethyl)-γ-oxo-p-chloro-homophenylalanine as a white precipitate. The yield was 85%. The diastereomer ratio ((αS,1S) form/(αR,1S) form) was not less than 99/1. The precipitate collected by filtration was recrystallized from acetonitrile-water to give (αS,1S)-N-(1-phenethyl)-γ-oxo-p-chloro-homophenylalanine as white needle crystals.

TLC (silica gel); Rf=0.65 (n-butanol:acetic acid:water=4:1:1).

NMR (DMSO-$d_6$+trifluoroacetic acid, δ): 7.9 (d, J=8.8, 2H), 7.6 (d, J=8.8, 2H), 7.5 (m, 5H), 4.6 (q, J=6.8, 1H), 3.9 (m, 1H), 3.6 (m, 2H), 1.6 (d, J=6.8, 3H).

IR (KBr disk, cm$^{-1}$): 1700, 1630, 1610, 1580, 1570, 1370.

Melting point: 172 to 174° C. $[α]^{20}_D$=+24.0 (c=0.10, $CH_3CN$:TFA=99:1, v/v).

Elemental analysis: Found: C, 65.01; H, 5.53; N, 4.32; Calculated: C, 65.16; H, 5.47; N, 4.22.

EXAMPLE 25

Synthesis of (αS,1S)-N-(1-phenethyl)-γ-oxo-p-methyl-homophenylalanine

Trans-p-methyl-β-benzoylacrylic acid (190 mg) was dissolved in 5 mL of ethanol, and the temperature was adjusted to 60° C. (S)-1-Phenethylamine (144 mg, 1.2 equivalents) was added, and the reaction was carried out at 60° C. for 6 hours. The resulting precipitate was filtered off and dried under vacuum to give 299 mg of (αS,1S)-N-(1-phenethyl)-γ-oxo-p-methyl-homophenylalanine as a white precipitate. The yield was 95%. The diastereomer ratio ((αS,1S) form/(αR,1S) form) was not less than 97/3. The precipitate collected by filtration was recrystallized from acetonitrile-water to give (αS,1S)-N-(1-phenethyl)-γ-oxo-p-methyl-homophenylalanine as white needle crystals.

TLC (silica gel); Rf=0.60 (n-butanol:acetic acid:water=4:1:1).

NMR (DMSO-$d_6$+trifluoroacetic acid, δ): 7.9 (d, J=8.5, 2H), 7.5 (m, 5H), 7.4 (d, J=8.5, 2H), 4.6 (q, J=6.4, 1H), 3.9 (m, 1H), 3.6 (m, 2H), 2.4 (s, 3H), 1.6 (d, J=6.4, 3H).

IR (KBr disk, cm$^{-1}$): 1680, 1630, 1610, 1570, 1560, 1370.

Melting point: 205 to 207° C. $[α]^{20}_D$=+33.0 (c=0.10, $CH_3CN$:TFA=99:1, v/v).

Elemental analysis: Found: C, 73.21; H, 6.94; N, 4.49; Calculated: C, 73.29; H, 6.80; N, 4.50.

EXAMPLE 26

Synthesis of (αS,1S)-N-(1-phenethyl)-γ-oxo-p-nitro-homophenylalanine

Trans-p-nitro-β-benzoylacrylic acid (221 mg) was dissolved in 5 mL of ethanol, and the temperature was adjusted to 60° C. (S)-1-Phenethylamine (144 mg, 1.2 equivalents) was added, and the reaction was carried out at 60° C. for 6 hours. The resulting precipitate was filtered off and dried under vacuum to give 290 mg of (αS,1S)-N-(1-phenethyl)-γ-oxo-p-nitro-homophenylalanine as a yellow precipitate. The yield was 85%. The diastereomer ratio ((αS,1S) form/(αR,1S) form) was not less than 95/5. The precipitate collected by filtration was recrystallized from acetonitrile-water to give (αS,1S)-N-(1-phenethyl)-γ-oxo-p-nitro-homophenylalanine as yellow needle crystals.

TLC (silica gel); Rf=0.60 (n-butanol:acetic acid:water=4:1:1).

NMR (DMSO-d$_6$+trifluoroacetic acid, δ): 8.4 (d, J=8.6, 2H), 8.2 (d, J=8.6, 2H), 7.5 (m, 5H), 4.6 (q, J=6.8, 1H), 4.0 (m, 1H), 3.7 (m, 2H), 1.6 (d, J=6.8, 3H).

IR (KBr disk, cm$^{-1}$): 1700, 1630, 1570, 1520, 1380, 1350.

Melting point: 152 to 154° C. [α]$^{20}_D$=+23.0 (c=0.10, CH$_3$CN:TFA=99:1, v/v).

Elemental analysis: Found: C, 63.28; H, 5.36; N, 8.06; Calculated: C, 63.15; H, 5.30; N, 8.18.

EXAMPLE 27

Synthesis of (αS,1S)-N-(1-phenethyl)-γ-oxo-p-fluoro-homophenylalanine

Trans-p-fluoro-β-benzoylacrylic acid (194 mg) was dissolved in 3 mL of methanol, and the temperature was adjusted to 60° C. (S)-1-Phenethylamine (144 mg, 1.2 equivalents) was added, and the reaction was carried out at 60° C. for 6 hours. The resulting precipitate was filtered off and dried under vacuum to give 190 mg of (αS,1S)-N-(1-phenethyl)-γ-oxo-p-fluoro-homophenylalanine as a white precipitate. The yield was 70%. The diastereomer ratio ((αS,1S) form/(αR,1S) form) was not less than 90/10. The precipitate collected by filtration was recrystallized from acetonitrile-water to give (αS,1S)-N-(1-phenethyl)-γ-oxo-p-fluoro-homophenylalanine as white needle crystals.

TLC (silica gel); Rf=0.65 (n-butanol:acetic acid:water=4:1:1).

NMR (DMSO-d$_6$+trifluoroacetic acid, δ): 8.0 (dd, J=8.3, 5.6, 2H), 7.5 (m, 5H), 7.4 (dd, J=8.3, 8.3, 2H), 4.6 (q, J=6.8, 1H), 4.0 (m, 1H), 3.6 (m, 2H), 1.6 (d, J=6.8, 3H).

IR (KBr disk, cm$^{-1}$): 1700, 1650, 1600, 1350, 1290, 1220, 1160.

Melting point: 175 to 177° C. [α]$^{20}_D$=+26.0 (c=0.10, CH$_3$CN:TFA=99:1, v/v).

Elemental analysis: Found: C, 68.65; H, 5.67; N, 4.29; Calculated: C, 68.56; H, 5.75; N, 4.44.

EXAMPLE 28

Synthesis of (αS,1S)-N-(1-phenethyl)-γ-oxo-p-phenyl-homophenylalanine

Trans-p-phenyl-β-benzoylacrylic acid (252 mg) was dissolved in 5 mL of methanol, and the temperature was adjusted to 60° C. (S)-1-Phenethylamine (144 mg, 1.2 equivalents) was added, and the reaction was carried out at 60° C. for 6 hours. The resulting precipitate was filtered off and dried under vacuum to give 320 mg of (αS,1S)-N-(1-phenethyl)-γ-oxo-p-phenyl-homophenylalanine as a white precipitate. The yield was 87%. The diastereomer ratio ((αS,1S) form/(αR,1S) form) was not less than 95/5. The precipitate collected by filtration was recrystallized from acetonitrile-water to give (αS,1S)-N-(1-phenethyl)-γ-oxo-p-phenyl-homophenylalanine as white needle crystals.

TLC (silica gel); Rf=0.80 (n-butanol:acetic acid:water=4:1:1).

NMR (DMSO-d$_6$+trifluoroacetic acid, δ): 8.0 (d, J=8.2, 2H), 7.9 (d, J=8.2, 2H), 7.8 (d, J=8.3, 2H), 7.5 (m, 8H), 4.6 (q, J=6.8, 1H), 4.0 (m, 1H), 3.7 (m, 2H), 1.6 (d, J=6.8, 3H).

IR (KBr disk, cm$^{-1}$): 1680, 1640, 1620, 1510, 1380.

Melting point: 183 to 185° C. [α]$^{20}_D$=+42.0 (c=0.10, CH$_3$CN:TFA=99:1, v/v).

Elemental analysis: Found: C, 77.24; H, 6.11; N, 3.91; Calculated: C, 77.19; H, 6.21; N, 3.75.

EXAMPLE 29

Synthesis of (αS,1S)-N-(1-phenethyl)-γ-oxo-p,m-dimethoxy-homophenylalanine

Trans-p,m-dimethoxy-β-benzoylacrylic acid (236 mg) was dissolved in 5 mL of methanol, and the temperature was adjusted to 60° C. (S)-1-Phenethylamine (144 mg, 1.2 equivalents) was added, and the reaction was carried out at 60° C. for 6 hours. The resulting precipitate was filtered off and dried under vacuum to give 286 mg of (αS,1S)-N-(1-phenethyl)-γ-oxo-p,m-dimethoxy-homophenylalanine as a white precipitate. The yield was 80%. The diastereomer ratio ((αS,1S) form/(αR,1S) form) was not less than 95/5. The precipitate collected by filtration was recrystallized from acetonitrile-water to give (αS,1S)-N-(1-phenethyl)-γ-oxo-p,m-dimethoxy-homophenylalanine as white needle crystals.

TLC (silica gel); Rf=0.70 (n-butanol:acetic acid:water=4:1:1).

NMR (DMSO-d$_6$+trifluoroacetic acid, δ): 7.6 (d,J=8.5, 1H), 7.5 (m, 5H), 7.1 (d, J=8.5, 2H), 4.6 (q, J=6.8, 1H), 3.9 (m, 1H), 3.9 (s, 3H), 3.8 (s, 3H), 3.6 (m, 2H), 1.6 (d, J=6.8, 3H).

IR (KBr disk, cm$^{-1}$): 1680, 1620, 1590, 1570, 1510, 1460, 1420, 1380, 1270.

Melting point: 171 to 173° C. [α]$^{20}_D$=+34.0 (c=0.10, CH$_3$CN:TFA=99:1, v/v).

Elemental analysis: Found: C, 67.08; H, 6.66; N, 3.83; Calculated: C, 67.11; H, 6.49; N, 3.92.

EXAMPLE 30

Synthesis of (R)-p-methoxy-homophenylalanine

To 10 mL of ethanol was added 10 mL of 0.5 N sulfuric acid, and 327 mg of (αR,1R)-N-(1-phenethyl)-γ-oxo-p-methoxy-homophenylalanine was added thereto and dissolved therein. To this mixed solution was added 50 mg of 10% palladium-carbon, and hydrogenation was carried out at 20° C. and atmospheric pressure with stirring. After the reaction, the catalyst was filtered off under suction, the solvent was distilled off, and the white solid thus obtained was subjected to reversed phase HPLC to give 105 mg of (R)-p-methoxy-homophenylalanine. The yield was 50%.

TLC (silica gel); Rf=0.37 (n-butanol:acetic acid:water=4:1:1).

NMR (D$_2$O, HCl form, δ): 7.1 (d, J=7.3, 2H), 6.8 (d, J=7.3, 2H), 3.9 (t, J=6.8, 1H), 3.7 (s, 3H), 2.6 (m, 2H), 2.1 (m, 2H).

Melting point: 234° C. [α]$^{20}_D$=−30.6 (c=0.1, 5 M HCl).

The above data were in complete agreement with those for (R)-p-methoxy-homophenylalanine synthesized by the process described in the Bulletin of the Chemical Society of Japan, vol. 55, page 918 (1982).

EXAMPLE 31

Synthesis of (S)-p-methoxy-homophenylalanine

To 10 mL of ethanol was added 10 mL of 0.5 N sulfuric acid, and 163 mg of (αS,1S)-N-(1-phenethyl)-γ-oxo-p-methoxy-homophenylalanine was added thereto and dissolved therein. To this mixed solution was added 40 mg of 10% palladium-carbon, and hydrogenation was carried out at 50° C. under 5 atmospheres with stirring. After the reaction, the catalyst was filtered off under suction, the solvent was distilled off, and the solid obtained was recrystallized from ethanol-water to give 84 mg of (S)-p-methoxy-homophenylalanine as white cubic crystals. The yield was 80%.

TLC (silica gel); Rf=0.37 (n-butanol:acetic acid:water=4:1:1).

NMR (D$_2$O, HCl form, δ): 7.1 (d, J=7.3, 2H), 6.8 (d, J=7.3, 2H), 3.9 (t, J=6.8, 1H), 3.7 (s, 3H), 2.6 (m, 2H), 2.1 (m, 2H).

Melting point: 234° C. $[\alpha]^{20}_D$=+30.8 (c=0.1, 5 M HCl).

The above data were in complete agreement with those for (S)-p-methoxy-homophenylalanine synthesized by the process described in the Bulletin of the Chemical Society of Japan, vol. 55, page 918 (1982).

EXAMPLE 32

Synthesis of (S)-homophenylalanine

To 10 mL of ethanol was added 10 mL of 0.5 N sulfuric acid, and 298 mg of ($\alpha$S,1S)-N-(1-phenethyl)-$\gamma$-oxo-homophenylalanine was added thereto and dissolved therein. To this mixed solution was added 30 mg of 10% palladium-carbon, and hydrogenation was carried out at 20° C. under 5 atmospheres with stirring. After the reaction, the catalyst was filtered off under suction, the solvent was distilled off, and the solid obtained was recrystallized from ethanol-water to give 125 mg of (S)-homophenylalanine as white needle crystals. The yield was 70%.

TLC (silica gel); Rf=0.34 (n-butanol:acetic acid:water= 4:1:1).

NMR ($D_2O$, HCl form, $\delta$): 7.2 (m, 5H), 3.9 (t, J=6.8,1H), 2.6 (m, 2H), 2.1 (m, 2H).

The optical rotation was measured after conversion to the methyl ester by the method described in the Journal of Organic Chemistry, vol. 55, page 5567 (1990). $[\alpha]^{20}_D$=+44.5 (c=1.0, 0.1 M HCl).

The above data were in complete agreement with those for (S)-homophenylalanine produced by the process described in the Journal of Biological Chemistry, vol. 122, number 348 (pages 1937 to 1938).

INDUSTRIAL APPLICABILITY

The $\gamma$-oxo-homophenylalanine derivative of the present invention is as mentioned hereinabove and, therefore, the optically active homophenylalanine derivatives (IV) can be obtained therefrom by an economically excellent and efficient production process.

We claim:

1. A $\gamma$-oxo-homophenylalanine derivative of the general formula (I):

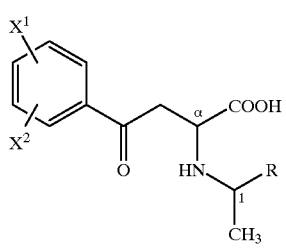

(I)

(wherein $X^1$ and $X^2$ are the same or different and each represents a hydrogen atom, an alkyl group containing 1 to 7 carbon atoms, an aryl group containing 6 to 10 carbon atoms, an aralkyl group containing 7 to 10 carbon atoms, a hydroxyl group, a halogen atom, a cyano group, a trifluoromethyl group, an alkoxyl group containing 1 to 4 carbon atoms, an alkylmercapto group containing 1 to 4 carbon atoms or a nitro group; and R represents a phenyl group, a substituted phenyl group or a naphthyl group).

2. A $\gamma$-oxo-homophenylalanine derivative according to claim 1, wherein $X^1$ is a p-methoxy group and $X^2$ is a hydrogen atom.

3. A $\gamma$-oxo-homophenylalanine derivative according to claim 1, wherein $X^1$ is a hydrogen atom and $X^2$ is a hydrogen atom.

4. A $\gamma$-oxo-homophenylalanine derivative according to claim 1, wherein R is a phenyl group.

5. A $\gamma$-oxo-homophenylalanine derivative according to claim 1, wherein the configuration is ($\alpha$R,1R).

6. A $\gamma$-oxo-homophenylalanine derivative according to claim 1, wherein the configuration is ($\alpha$S,1S).

7. A $\gamma$-oxo-homophenylalanine derivative according to claim 1, which occurs as a mixture of the $\gamma$-oxo-homophenylalanine derivative having the ($\alpha$R,1R) configuration and the $\gamma$-oxo-homophenylalanine derivative having the ($\alpha$S,1R) configuration.

8. A $\gamma$-oxo-homophenylalanine derivative according to claim 1, which occurs as a mixture of the $\gamma$-oxo-homophenylalanine derivative having the ($\alpha$S,1S) configuration and the $\gamma$-oxo-homophenylalanine derivative having the ($\alpha$R,1S) configuration.

9. A process for producing a $\gamma$-oxo-homophenylalanine derivative of the general formula (I):

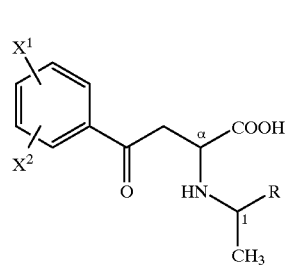

(I)

(wherein $X^1$ and $X^2$ are the same or different and each represents a hydrogen atom, an alkyl group containing 1 to 7 carbon atoms, an aryl group containing 6 to 10 carbon atoms, an aralkyl group containing 7 to 10 carbon atoms, a hydroxyl group, a halogen atom, a cyano group, a trifluoromethyl group, an alkoxyl group containing 1 to 4 carbon atoms, an alkylmercapto group containing 1 to 4 carbon atoms or a nitro group; and R represents a phenyl group, a substituted phenyl group or a naphthyl group) which comprises reacting a $\gamma$-benzoylacrylic acid derivative of the general formula (II):

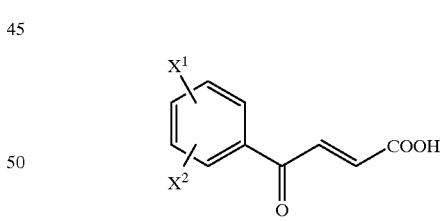

(II)

(wherein $X^1$ and $X^2$ are as defined above) with a 1-arylethylamine derivative of the general formula (III):

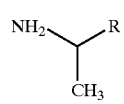

(III)

(wherein R is as defined above).

10. A process for producing a $\gamma$-oxo-homophenylalanine derivative according to claim 9, wherein a $\beta$-benzoylacrylic acid derivative in which $X^1$ is a p-methoxy group and $X^2$ is a hydrogen atom is used.

11. A process for producing a γ-oxo-homophenylalanine derivative according to claim 9, wherein a β-benzoylacrylic acid derivative in which X¹ is a hydrogen atom and X² is a hydrogen atom is used.

12. A process for producing a γ-oxo-homophenylalanine derivative according to claim 9, wherein the 1-arylethylamine derivative is 1-phenethylamine.

13. A process for producing a γ-oxo-homophenylalanine derivative according to claim 12, wherein the 1-phenethylamine is in the (S) form or (R) form.

14. A process for producing a γ-oxo-homophenylalanine derivative according to claim 9, wherein an alcohol solvent is used as the reaction solvent.

15. A process for producing a homophenylalanine derivative of the general formula (IV):

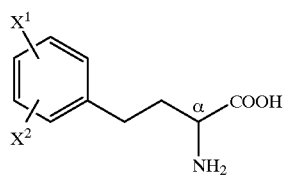

(IV)

(wherein X¹ and X² are the same or different and each represents a hydrogen atom, an alkyl group containing 1 to 7 carbon atoms, an aryl group containing 6 to 10 carbon atoms, an aralkyl group containing 7 to 10 carbon atoms, a hydroxyl group, a halogen atom, a cyano group, a trifluoromethyl group, an alkoxyl group containing 1 to 4 carbon atoms, an alkylmercapto group containing 1 to 4 carbon atoms or a nitro group) which comprises subjecting a γ-oxo-homophenylalanine derivative of the general formula (I):

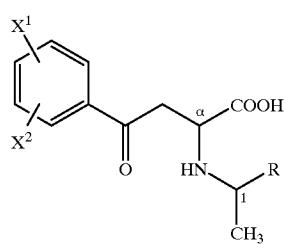

(I)

(wherein X¹ and X² are as defined above and R represents a phenyl group, a substituted phenyl group or a naphthyl group) to reduction reaction.

16. A process for producing a homophenylalanine derivative according to claim 15, wherein a γ-oxo-homophenylalanine derivative having the (αR,1R) configuration is used to produce the corresponding homophenylalanine derivative having the (R) configuration at the α position.

17. A process for producing a homophenylalanine derivative according to claim 15, wherein a γ-oxo-homophenylalanine derivative having the (αS,1S) configuration is used to produce the corresponding homophenylalanine derivative having the (S) configuration at the α position.

18. A process for producing a homophenylalanine derivative according to claim 15, wherein the reduction reaction is carried out in the presence of the metal catalyst.

19. A process for producing a homophenylalanine derivative according to claim 15, wherein hydrogen is used as the reducing agent.

20. A process for producing a homophenylalanine derivative according to claim 15, wherein a formic acid salt is used as the reducing agent.

21. A process for producing a homophenylalanine derivative according to claim 18, wherein the metal catalyst is a palladium catalyst.

22. A process for producing a homophenylalanine derivative according to claim 15, wherein the reduction reaction is carried out in an alcohol solvent containing a mineral acid.

23. A process for producing a homophenylalanine derivative of the general formula (IV):

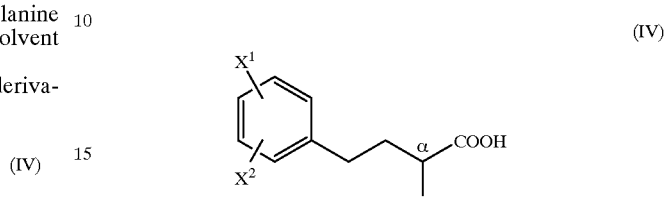

(IV)

(wherein X¹ and X² are the same or different and each represents a hydrogen atom, an alkyl group containing 1 to 7 carbon atoms, an aryl group containing 6 to 10 carbon atoms, an aralkyl group containing 7 to 10 carbon atoms, a hydroxyl group, a halogen atom, a cyano group, a trifluoromethyl group, an alkoxyl group containing 1 to 4 carbon atoms, an alkylmercapto group containing 1 to 4 carbon atoms or a nitro group) which comprises reacting a β-benzoylacrylic acid derivative of the general formula (II):

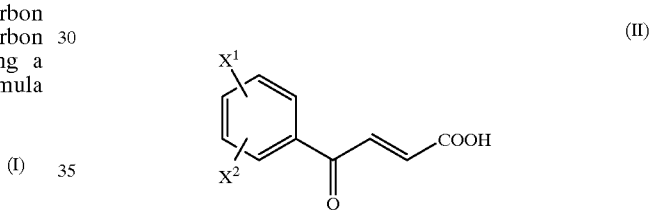

(II)

(wherein X¹ and X² are as defined above) with a 1-arylethylamine derivative of the general formula (III):

(III)

(wherein R represents a phenyl group, a substituted phenyl group or a naphthyl group) and subjecting to reduction reaction the resulting γ-oxo-homophenylalanine derivative of the general formula (I):

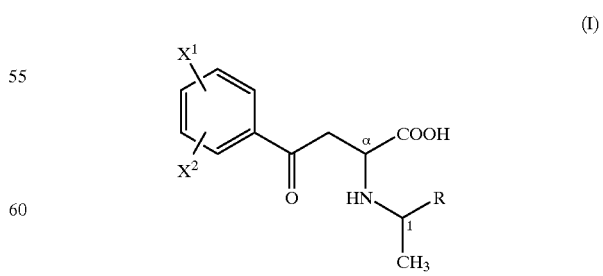

(I)

(wherein X¹, X² and R are as defined above).

* * * * *